United States Patent [19]  
Rothfuss et al.

[11] Patent Number: 4,487,394  
[45] Date of Patent: Dec. 11, 1984

[54] EXTRACTOR FOR SURGICAL STAPLES

[75] Inventors: Robert G. Rothfuss, Bellevue, Ky.; David K. Kuhl, Cincinnati, Ohio

[73] Assignee: Senco Products, Inc., Cincinnati, Ohio

[21] Appl. No.: 368,100

[22] Filed: Apr. 14, 1982

[51] Int. Cl.³ .................. B25C 11/00; A61B 17/04
[52] U.S. Cl. ................................. 254/28; 128/334 R
[58] Field of Search .................. 128/334 R, 318, 319, 128/321; 227/DIG. 1, 63, 19; 254/28

[56] References Cited

U.S. PATENT DOCUMENTS

| 2,202,984 | 6/1940 | Drypolcher | 254/28 |
| 2,470,726 | 5/1949 | Schafroth et al. | 254/28 |
| 2,481,647 | 9/1949 | de Generes | 254/28 |
| 4,026,520 | 5/1977 | Rothfuss | 254/28 |

FOREIGN PATENT DOCUMENTS

| 0059778 | 9/1982 | European Pat. Off. | 254/28 |
| WO83/00428 | 2/1983 | PCT Int'l Appl. | 254/28 |

Primary Examiner—Dalton L. Truluck  
Assistant Examiner—Gene B. Kartchner  
Attorney, Agent, or Firm—Frost & Jacobs

[57] ABSTRACT

A manually actuated surgical staple extractor comprising upper and lower handles pivotally joined together and swingable between open and closed positions. The upper handle terminates at its forward end in a pair of thin, flat, laterally extending stops separated by a blade-receiving slot. The forwardmost portions of the stops lie in an obtuse angle to the upper handle and are joined together by a thin, coplanar, forwardly projecting, U-shaped anvil. The lower handle terminates in a thin blade. When the handles are in their open positions, the blade is located in the above noted slot with its lower edge above the anvil. When the handles are shifted toward each other to their closed positions, the blade pivots downwardly so that it passes through the U-shaped anvil to a position therebelow. The blade and the anvil are so configured that, as the blade passes through the anvil, there is clearance therebetween to either side of the blade, the clearance being at least equal to the diameter of the crown portion of the staple.

16 Claims, 11 Drawing Figures

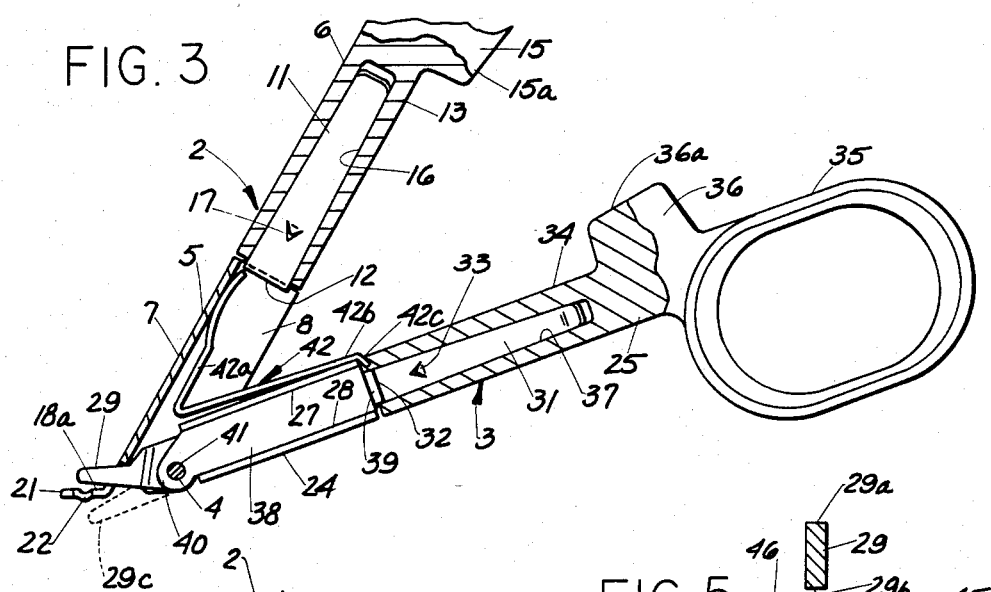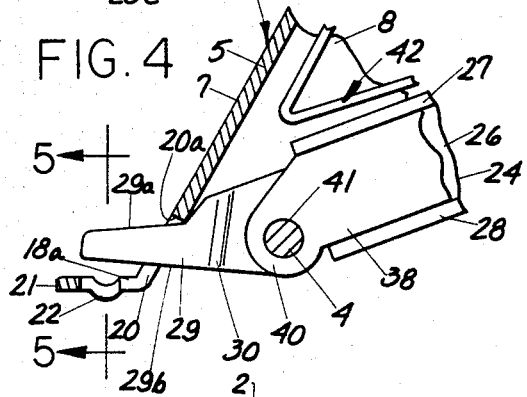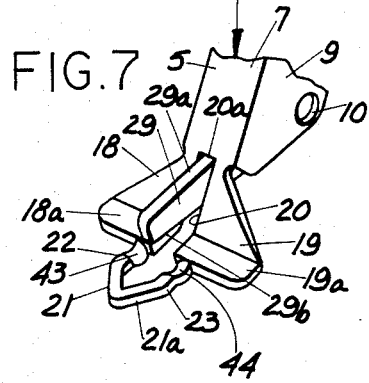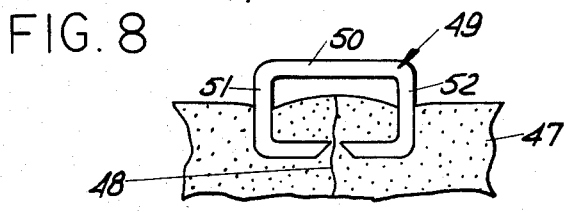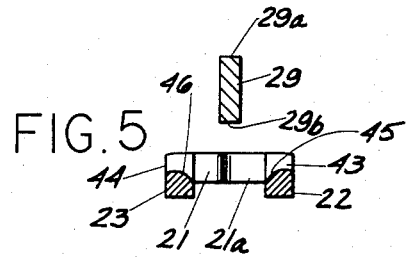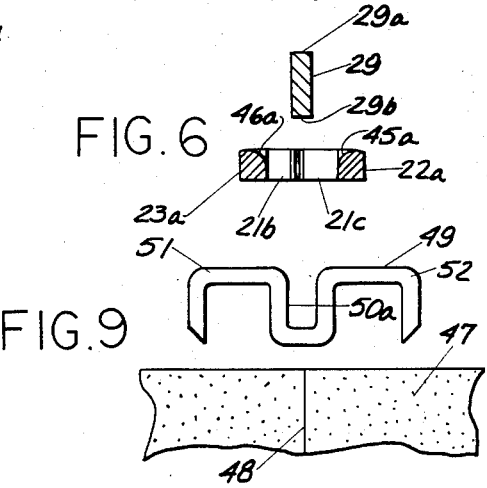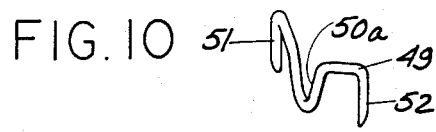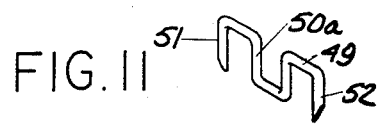

EXTRACTOR FOR SURGICAL STAPLES

TECHNICAL FIELD

The invention relates to an extractor for surgical staples, and more particularly to a manually operated extractor capable of removing surgical staples with greater ease and less trauma to the patient.

BACKGROUND ART

In recent years surgeons have turned more and more to the use of surgical staples, rather than conventional thread sutures, for closing wounds or incisions in the skin or fascia of a patient. This is true, in part, because the stapling operation is a simpler procedure in many instances. More importantly, however, is the fact that the stapling procedure is very much faster than conventional thread suturing. Thus, particularly in those instances where a large number of sutures is required, the length of time for the suturing procedure and the length of time the patient must be maintained under anesthesia are greatly reduced when surgical staples are used.

U.S. Pat. Nos. 3,643,851; 3,717,294; and 3,837,555 illustrate typical surgical staples. A staple of the type shown in these patents initially has an elongated crown terminating in downwardly depending leg portions. The free ends of the downwardly depending leg portions are provided with downwardly and outwardly sloping cuts, forming points. During the forming and implanting of such a staple in the skin or fascia of a patient by a surgical stapling instrument, end portions of the elongated crown are bent downwardly. This results in a staple with a narrower crown and L-shaped legs, the pointed ends of which are opposed, and the L-shaped legs being embedded in the patient's skin or fascia.

Another type of surgical staple is taught in U.S. Pat. No. 4,014,492. This staple initially comprises a central crown portion terminating at either end in portions sloping upwardly and outwardly, these upwardly and outwardly sloping portions, in turn, terminating in downwardly and outwardly sloping portions. The last mentioned portions are provided with cut surfaces forming points. The cut surfaces initially lie in a position substantially perpendicular to the staple crown and the skin or fascia of the patient to be joined. During forming and implanting of this type of staple, the upwardly and outwardly sloping portions of the staple, at their junction with the crown, are bent downwardly to form a staple having a crown and L-shaped legs, the points of which are opposed.

Either type of surgical staple described above can be removed from the skin or fascia of the patient by bending the staple crown into a U-shaped configuration. This will cause the L-shaped legs of the formed staple to shift upwardly and outwardly so that they may be lifted from the patient's skin or fascia.

Prior art workers having developed manual extractors for bending the crown of surgical staples and lifting the staple from the patient's skin. In its typical form, a prior art extractor comprises a pliers-like tool having first and second handle means pivoted together and formed of sheet metal. The first handle means terminates in a pair of anvils in parallel-spaced relationship. The anvils are provided at their rearward ends with notches so that, when the anvils are slipped under the crown portion of a surgical staple, the crown will be received in the notches.

The second handle of the extractor generally is provided with a relatively thick, two-ply, blade-like forward end substantially as long or longer than the anvils. When the handle elements of the extractor are in their open position, this blade lies above the anvils and the notches therein. As the handle elements are shifted to their closed positions, the blade element passes between the anvils and the notches therein making the above described U-shaped bend in the staple crown located in the notches.

In the use of an extractor of this type, the anvils (when slipped beneath the crown of a staple) will rub against traumatized areas of the skin, causing pain to the patient. Since the blade portion of the extractor is as long or longer than the anvils, it partially obscures the anvils, making their proper insertion under the staple crown and location of the staple crown in the anvil notches more difficult. Furthermore, when the extractor anvils are parallel throughout their length, the operator may inadvertently slip only one anvil under the crown of the staple to be extracted. Under these circumstances, the staple will not properly open and if the operator pulls the extractor upwardly the patient will undergo severe pain.

When such a prior art extractor is actuated to bend the crown of a surgical staple, clearance between the blade and the anvils is such that the crown tends to make the anvils spread apart, further irritating the traumatized skin. As a further consequence, the legs of the U-shaped bend in the staple crown are generally non-parallel, with the result that the staple legs themselves are not fully opened. In addition, such extractors are generally constructed in such a way that the first handle element can inadvertently become "flipped" (or pivoted through more than 180°) with respect to the second handle element, thus rendering the extractor useless until its handle elements are returned to their proper orientation. Frequently, such prior art extractors are provided with means to bias the handle elements to their open position. This biasing means can become dislocated, tending to jam the extractor.

U.S. Pat. No. 4,026,520 teaches a manually operated surgical staple extractor of pliers-like form and having first and second handle elements pivotally joined together near their forward ends. These handle elements are manually shiftable between open and closed positions and may be biased to their open position. The biasing means is so configured that it cannot become dislocated and jam the extractor. Furthermore, means are provided to prevent one handle from becoming "flipped" with respect to the other.

The first handle element of the extractor of U.S. Pat. No. 4,026,520 is bifurcated at its forward end, the bifurcations terminating in a pair of elongated anvils in parallel-spaced relationship with the forward ends of these anvils angled toward each other so that the frontmost tips thereof are contiguous or nearly so. At the rearward ends, the anvils are provided with aligned notches to receive the crown of a staple. The bifurcations of the first handle element provide a steep upwardly and rearwardly sloping surface adjacent each of the anvil notches to assist in and ensure the location of the staple crown in the notches.

A thin blade means is located between the bifurcations of the first handle element and is operatively connected to the forward end of the second handle element.

The blade means has a nose portion shorter than the anvils and a lower edge adapted to produce a U-shaped bend in the crown of a staple located in the anvil notches. The blade nose portion is shiftable by the second handle element between a first position (when the handle elements are in their open position) wherein the lower edge of the nose lies above the anvils and the notches therein, and a second position (when the handle elements are in their closed position) wherein the nose lies between the anvils with the lower edge of the nose located below the anvils. The anvils are so spaced from each other and the nose of the blade means is sufficiently thin that clearance is provided between the nose and each anvil substantially equal to the diameter of the crown portion of the surgical staple being extracted. As a result, the anvils do not tend to spread during an extracting procedure and the surgical staple legs are fully opened.

U.S. Pat. No. 4,026,520 teaches two embodiments of the extractor. In one embodiment, the blade comprises an integral one-piece part of the second handle element. In the other embodiment, the blade is a separate element pivotally mounted between the bifurcations of the first handle element and operatively connected to the forward end of the second handle element.

While the extractor of U.S. Pat. No. 4,026,520 represents a considerable advance in the art, it still is characterized by certain deficiencies. First of all, the anvil portions are of considerable thickness, causing trauma when slipped beneath the crown of a surgical staple, especially when the staple is embedded. Furthermore, as is true of other prior art extractors, the extractor of U.S. Pat. No. 4,026,520 has a tendency to bend a surgical staple in more than one plane during the extracting procedure, again increasing the trauma experienced by the patient.

The extractor of the present invention is intended to overcome the problems encountered with prior art extractors and to constitute an improvement thereover. Its construction is simple and inexpensive so that, while it may be manufactured as a reusable and resterilizable tool, it lends itself well to being produced in the form of a single-use, disposable tool. The extractor is characterized by a one-piece, horizontal anvil, slightly pointed at its forwardmost end and of minimal thickness to greatly reduce the trauma in placing the anvil under the staple crown. The anvil is provided with means for positive and exact positioning of the staple crown to prevent slipping while reforming the extracting a staple. The reforming of the surgical staple is accomplished substantially in a single plane and in the configuration of the anvil, together with the provision of a thin blade, makes it possible to achieve parallel staple legs during the reforming and extracting process. This enables the legs to be lifted from the skin or fascia of the patient with minimal discomfort. The handle portions are provided with scissors-like, finger-engaging loops designed to lend the extractor stability during the extracting procedure. The handles are provided with stops giving the surgeon a positive tactile feedback when the staple is properly reformed, and insuring that each staple is identically reformed. A novel method of attaching the looped handles to the instrument is taught. Preferably, spring means are provided to bias the handles to their open positions. The spring is so mounted that it cannot be dislocated, and thus cannot jam the extractor. The combination of the blade of the lower handle and the slotted forward end of the upper handle prevent the possibility of one handle becoming "flipped" with respect to the other. A plastic insert takes up the slack between the handle elements at the point at which they are pivoted together, lending a firm and positive scissoring action to the instrument. Finally, while the instrument could be made of materials such that it could be reused and resterilized, it can be manufactured quite inexpensively, lending itself well to being a single-use, disposable instrument. The instrument also lends itself well to appropriate presterile packaging.

DISCLOSURE OF THE INVENTION

According to the invention there is provided a manually actuated surgical staple extractor. The extractor comprises upper and lower handles, pivotally joined together and swingable between open and closed positions. Both handles terminate at their rearward ends in scissor-like looped elements provided with cooperating stops to determine the closed positions of the handles.

The upper handle terminates at its forward end in a pair of thin, flat, laterally (or transversely) extending stops separated by a blade-receiving slot. The forwardmost portions of the stops lie at an obtuse angle to the first handle and are joined together by an integral, thin, coplanar, forwardly-projecting, U-shaped anvil with the base portion of the U-shaped anvil being slightly pointed to facilitate insertion beneath the crown of an implanted surgical staple. The laterally extending stops prevent the anvil from being shoved too far beneath the crown of an implanted surgical staple and tend to ensure that the surgical staple is reformed in a single plane. At the juncture of the legs of the anvil and the lateral stops, the legs may be provided with aligned notches adapted to receive the crown of the implanted surgical staple to assure proper location thereof with respect to the anvil.

The lower handle terminates in a thin blade. The upper edge of the blade cooperates with the blade receiving slot of the forward end of the upper handle to determine the openmost positions of the handles. When the handles are in their open positions, the blade is located wholly above the anvil. When the handles are shifted toward each other to their closed positions, the blade pivots downwardly so that it passes through the U-shaped anvil, between the legs thereof. The blade and the anvil are so configured that, as the blade passes through the anvil, there is clearance therebetween to either side of the blade at least equal to the diameter of the crown portion of the staple. This, in conjunction with the travel of the blade (as determined by the above mentioned stops), results in the fact that the legs of the reformed surgical staple are substantially parallel so that they can be lifted from the skin or fascia of the patient with minimal discomfort. The extractor can be manufactured as a single-use, disposable instrument, as will be described hereinafter.

BRIEF DESCRIPTION OF THE DRAWINGS

FIG. 3 is a fragmentary side elevational view, partly in cross-section.

FIG. 4 is a fragmentary enlarged view (partly in cross-section) of the forward end of the instrument as seen in FIG. 3.

FIG. 5 is a cross-sectional view taken along section line 5—5 of FIG. 4.

FIG. 6 is a cross-sectional view similar to FIG. 5, but illustrating an anvil without aligned notches.

FIG. 7 is a fragmentary perspective view of the forward end of the extractor.

FIG. 8 is a fragmentary view illustrating a surgical staple implanted in a patient's skin and closing a wound therein.

FIG. 9 is a fragmentary view, similar to FIG. 8 but illustrating the surgical staple having been extracted.

FIG. 10 is a perspective view illustrating an extracted surgical staple which has been reformed in more than one plane.

FIG. 11 is a perspective view, similar to FIG. 10, but illustrating a surgical staple having been reformed in a single plane.

DETAILED DESCRIPTION OF THE INVENTION

Figure 1:
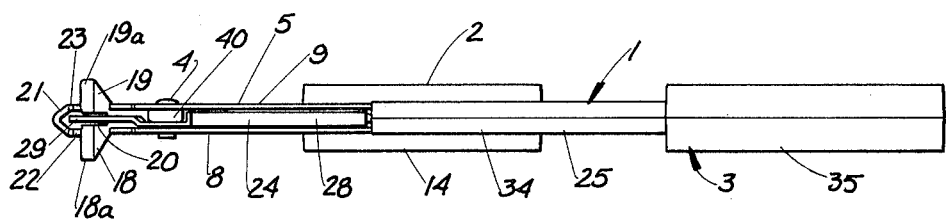
FIG. 1 is a bottom view of the extractor of the present invention.
Figure 2:
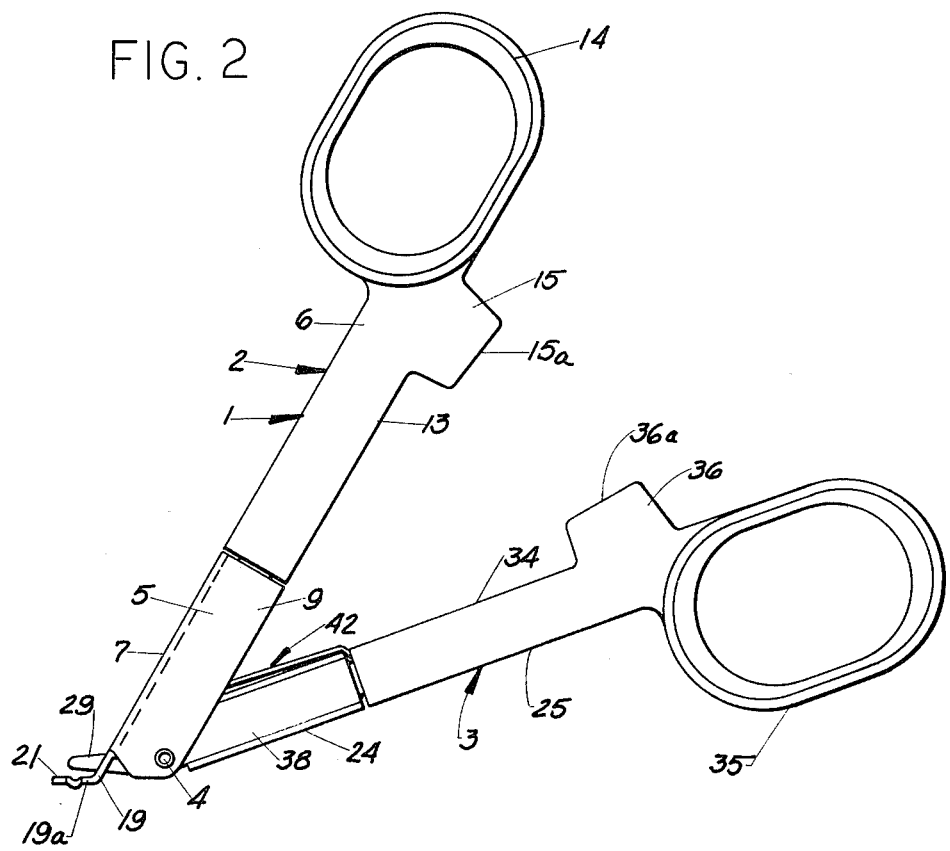
FIG. 2 is a side elevational view of the extractor of FIG. 1.

The extractor of the present invention is best illustrated in FIGS. 1 and 2 and is generally indicated at 1 therein. The extractor 1 has an upper handle generally indicated at 2 and a lower handle generally indicated at 3. Handles 2 and 3 are pivotally joined together near their forward ends by pivot pin 4.

Upper handle 2 has a first metallic part 5 and a second plastic part 6. The major portion of the metallic part 5 is of inverted U-shaped configuration having a base 7 and downwardly depending leg portions 8 and 9 (see also FIGS. 3 and 7). Near the forward end of the metallic portion 5 of upper handle 2, a pair of coaxial perforations are formed in the legs 8 and 9. The perforation in leg 9 is shown at 10 in FIG. 7. These perforations are adapted to accommodate pivot pin 4.

The rearward end of leg 8 of metallic portion 5 has a rearward extension 11 formed thereon (see FIG. 3). As is most clearly shown in FIG. 3, the extension 11 is inset at 12 from leg 8 so as to lie in a plane parallel to, but between the planes of legs 8 and 9. The purpose of extension 11 will be evident hereinafter.

The plastic portion 6 of upper handle 2 comprises a shank 13 constituting essentially a continuation of the metallic upper handle portion 5. The shank 13 terminates in a scissors-like loop 14, engagable by the thumb of the operator. At the juncture of shank 13 and loop 14, the plastic upper handle portion 6 has an integral, downwardly depending stop 15, provided with an abutment surface 15a. The purpose of stop 15 and abutment surface 15a will be described hereinafter.

The shank 13 of plastic upper handle portion 6 has an elongated, longitudinally extending cavity 16 formed therein (see FIG. 3). The cavity 16 and the metallic upper handle portion extension 11 are so sized and configured that the extension 11 is just nicely received in cavity 16, preferably with a friction fit. It will be noted from FIG. 3 that both extension 11 and cavity 16 are longitudinally tapered. To assure that extension 11 remains firmly within cavity 16, the extension may be provided with a small pointed tang 17 formed and slightly offset from the extension 11, itself. The tang 17 engages the inside surface of cavity 16 and precludes detachment of upper handle plastic portion 6 from upper handle metallic portion 5.

Reference is again made to FIGS. 1 and 7 in particular. From these figures it will be evident that the forwardmost end of the metallic portion 5 of upper handle 2 terminates in a pair of laterally extending stops 18 and 19, separated from each other by a slot 20. The laterally extending stops 18 and 19 constitute integral one-piece parts of the metallic portion 5 of upper handle 2, extending from the base 7 thereof.

Laterally extending stops 18 and 19 have forwardmost portions 18a and 19a, respectively, which are coplanar and lie at an angle to the main portions of lateral stops 18 and 19. The main portions of lateral stops 18 and 19 are coplanar with respect to each other and with respect to the base 7 of upper handle metallic portion 5. The angle between the main portions of stops 18 and 19 and their forwardmost portions 18a and 19a is an obtuse angle. While this angle may be varied, an angle of about 120° has been found suitable for ease of use by the operator.

A U-shaped anvil 21 extends forwardly from lateral stop portions 18a and 19a and constitutes an integral, one-piece part thereof. The U-shaped anvil 21 has a somewhat pointed base portion 21a and leg portions 22 and 23.

Lower handle 3 comprises a metallic portion 24 and a plastic portion 25. The main part of metallic portion 24 is of U-shaped configuration having a base 26 and laterally extending legs 27 and 28 (see FIG. 4).

The forward end of the lower handle metallic portion 24 is adapted to be received between the legs 8 and 9 of metallic upper handle portion 5 with the base 26 of lower handle metallic portion 24 lying adjacent and parallel to leg 8 of upper metallic handle portion 5.

The forward end of base 26 of lower handle metallic portion 24 terminates in a blade 29. Blade 29 is an integral, one-piece part of base 26. As can most clearly be seen in FIGS. 1 and 4, blade 29 is slightly offset as at 30 so as to lie in a plane parallel to but inset from the plane of base 26 of lower handle metallic portion 24. This also ensures that blade 29 will be centered with respect to slot 20 separating laterally extending stops 18 and 19 (see FIG. 7). The blade 29 has an upper edge 29a and a lower edge 29b.

Near its juncture with the base 26 of lower handle metallic portion 24, the blade 29 has a perforation (not shown) formed therein to accommodate pivot pin 4. In this way, upper handle 2 and lower handle 3 are pivotally joined together.

At its rearward end, the base portion 26 of the lower handle metallic portion 24 terminates in an extension 31 similar to the extension 11 of upper handle 2. The extension 31 constitutes an integral one-piece part of base 26 and is offset therefrom as at 32 so as to lie in a plane parallel to but slightly inset from that of base 26. The extension 31 may have an offset, pointed tine formed therein, as at 33.

The plastic portion 25 of lower handle 3 is similar to the upper handle plastic portion 6 and comprises an elongated shank 34 which substantially constitutes a continuation of lower handle metallic portion 24. The shank 34 terminates at its rearward end in a scissor-like loop 35, similar to loop 14 and adapted to be engaged by a finger of the operator. At the juncture of shank 34 and loop 35 there is an integral upwardly extending stop 36 on the plastic handle portion 25, having an abutment surface 36a adapted to cooperate with abutment surface 15a of upper handle plastic portion 6. As will be evident hereinafter, stops 15 and 36, when their surfaces 15a and 36a abut, determine the closed position of upper handle 2 and lower handle 3. In all of FIGS. 1, 2, 3 and 4, upper handle 2 and lower handle 3 are shown in their open positions. As can most clearly be discussed from FIG. 4, the open position of the handles is determined by the abutment of upper edge 29a of blade 29 against the end 20a of slot 20.

To attach the plastic portion 25 of lower handle 3 to the lower handle metallic portion 24, it is only necessary to insert extension 31 into the elongated, longitudinally extending cavity 37 formed in shank 34. Again, cavity 37 is so sized and configured as to just nicely receive extension 31, preferably with a frictional fit. Detachment of plastic portion 25 from extension 31 is precluded by tine 33. It will be understood that the attachment of plastic portions 6 and 25 to their respective extensions 11 and 31 could be accomplished in any other suitable manner, as for example, by insert molding.

In order to take up any play between upper handle 2 and lower handle 3 at the point of their pivoted connection, an insert 38 is used. The insert 38 is most clearly seen in FIGS. 3 and 4. Insert 38 comprises an elongated member just nicely received between the legs 27 and 28 of the lower handle metallic portion 24. At its rearward end, insert 38 is provided with a short tab 39 extending into the cavity 37 of plastic lower handle portion 25. At its forward end, insert 38 has a round nose portion 40 containing a perforation 41. The perforation 41 accommodates pivot pin 4 and the rounded nose portion 40 serves as a sort of washer for pivot pin 4. Preferably, insert 38 is made of the same plastic material as are plastic handle portions 6 and 25. It will be noted from FIG. 1 that pivot pin 4 may take the form of a rivet.

While not required, it is preferable that means be provided to urge or bias upper handle 2 and lower handle 3 to their open positions. Such a means is most clearly shown in FIG. 3 in the form of a leaf spring generally indicated at 42. Leaf spring 42 is substantially V-shaped, having a first leg 42a located between legs 8 and 9 of upper handle metallic portion 5 and bearing against the inside surface of the base 7 thereof. Leaf spring 42 has a second leg 42b which extends along the outside of leg 27 of lower handle metallic portion. The free end of leg 42b is bent downwardly as at 42c and extends between the lower handle metallic portion 24 and the lower handle plastic portion 25.

While not required, it is preferred that the anvil 21 be provided with a pair of aligned notches. Such notches are most clearly shown in FIG. 7 at 43 and 44, formed in the anvil legs 22 and 23, respectively, adjacent their juncture with laterally extending stop portions 18a and 19a. The aligned notches 43 and 44 are adapted to receive the crown of an implanted staple. Preferably, the upper inside edges of notches 43 and 44 are rounded, as at 45 and 46 (see FIG. 5) for reasons which will be evident hereinafter.

FIG. 6 is substantially identical to FIG. 5, but illustrates an anvil 21b having a base portion 21c and legs 22a and 23a. The anvil 21b differs from anvil 21 of FIG. 5 only in that its legs 22a and 23a are not provided with aligned notches. In this event, the upper inside edges of legs 22a and 23a are preferably rounded as at 45a and 46a, respectively, again for reasons which will be evident hereinafter.

The metallic parts of the extractor 1 are made from any appropriate metal (such as stainless steel) which is non-corrosive and sterilizable by any one or more of the standard methods. Similarly, the plastic parts are molded of non-toxic plastic material sterilizable by any one or more of the standard methods.

The extractor 1 having been described in detail, its operation can now be set forth. First, however, attention is turned to FIG. 8. In FIG. 8, the skin of a patient is illustrated at 47, having wound 48 formed therein. The wound is maintained in closed condition by a fully formed and implanted staple, generally indicated at 49. Such staples, together with the surgical stapling instruments by which they are formed and implanted, and the method by which they are formed and implanted, are all well known in the art. The formed and implanted staple 49 comprises a horizontal crown portion 50 terminating in L-shaped opposed legs 51 and 52, the free ends of which are pointed. As is well known to one skilled in the art, the verical portions of legs 51 and 52, as seen in FIG. 8, originally constituted parts of crown portion 50 and were coextensive therewith.

To remove the surgical staple 49 from the skin 47 of the patient, it is only necessary to bend or reform the crown portion 50 into a U-shape, as shown at 50a in FIG. 9. This makes the vertical portions of L-shaped legs 51 and 52 (as viewed in FIG. 8) become horizontal (as viewed in FIG. 9). This, in turn, results in the horizontal portions of legs 51 and 52 (as viewed in FIG. 8) becoming vertical (as viewed in FIG. 9). When the surgical staple 49 is properly reformed during the extracting process, the vertical portions of legs 51 and 52 should be substantially parallel so that they can be lifted from the skin 47 of the patient with a minimum of discomfort to the patient.

In the use of the extractor 1, the extractor is caused to approach the formed and implanted surgical staple 49 with its upper handle 2 and lower handle 3 in their open positions, as shown in FIGS. 1 through 4. The operator, having his thumb extending through loop 14 of handle 2 and a finger (such as the middle finger of the hand) extending through loop 35 of lower handle 3, simply maintains upper and lower handles 2 and 3 in their own positions. On the other hand, when a biasing means such as leaf spring 42 is used, the spring 42 may be employed to maintain or assist in maintaining handles 2 and 3 in their open positions.

With handles 2 and 3 in their open positions, it will be noted from the Figures that the lower edge 29b of blade 29 lies above anvil 21 and laterally extending stop portions 18a and 19a. This enables the anvil 21 to be inserted beneath the crown 50 of the formed and implanted staple 49 (see FIG. 8) until the vertical portions of legs 51 and 52 contact the forwardmost edges of laterally extending stop portions 18a and 19a. At this stage, the crown 50 of surgical staple 49 will be located in the aligned anvil notches 43 and 44, if such notches are present.

The fact that the base portion 21a of anvil 21 is somewhat pointed, and the fact that the anvil is thin (having a thickness equal to the gauge of the metal from which the upper handle metallic portion 5 is made), will greatly facilitate the slipping of the anvil 21 under the staple crown 50 with a minimum of discomfort to the patient, especially when the staple is embedded with crown 50 contacting skin 47. The forward portions 18a and 19a of laterally extending stops 18 and 19 will prevent the placing of anvil 21 too far under the staple crown 50. When notches 43 and 44 are provided in the anvil legs 22 and 23, they will be quite shallow and will tend to hold the staple crown in exact position, preventing slipping of anvil 21 with respect to staple crown 50 during the staple reforming procedure.

At this point, upper and lower handles 2 and 3 are squeezed together, causing lower handle 3 to approach upper handle 2 until the surface 36a of its stop 36 contacts the surface 15a of stop 15 of the upper handle 2. When upper and lower handles 2 and 3 are in their closed positions, the blade 29 will pass through slot 20 and anvil 21 to the position shown in broken lines at 29c in FIG. 3. This causes the crown 50 of formed and implanted surgical staple 49 to be bent into a U-shape as at 50a in FIG. 9. The fact that the anvil legs 22 and 23 are rounded in notches 43 and 44 as at 45 and 46 in FIG. 5 (or rounded as at 45a and 46a in the absence of notches 43 and 44, as in FIG. 6), will help facilitate the initial part of this crown bending procedure. The fact that blade 29 is only one thickness of sheet metal allows for a sharper crimp in staple crown 50, making it possible to achieve parallelism between the end portions of legs 51 and 52, as shown in FIG. 9, even with staples of maximum crown size. As is most clearly shown in FIG. 1, there is clearance to either side of blade 29 and the adjacent anvil legs 22 and 23. This clearance is at least equal to and preferably slightly greater than the diameter of the crown 50 of surgical staple 49. This ensures that surgical staples are reformed precisely the same time-after-time.

When the upper handle 2 and lower handle 3 are closed, the surgical staple 49 will achieve the configuration shown in FIG. 9. During the reforming of the surgical staple, the L-shaped legs 51 and 52 will begin to pull out of skin 47. When the free ends of the legs 51 and 52 are substantially parallel, the legs can be fully extracted from skin 47 with a minimum of discomfort to the patient.

The surgical staple of FIG. 9 is illustrated in perspective in both FIG. 10 and FIG. 11 and like parts have been given like index numerals. The illustration of FIG. 10 differs from that of FIG. 11 in that during the reforming step, the surgical staple 49 of FIG. 10 has been bent in more than one plane, so that the horizontal portions of legs 51 and 52 (as viewed in FIG. 10) are not substantially coaxial. In FIG. 11, however, the reformed staple has been bent in one plane only and the horizontal portions of legs 51 and 52 (as viewed in FIG. 11) are indeed substantially coaxial. A surgical staple, when reformed in one plane as shown in FIG. 11, offers far less discomfort to the patient during the extracting procedure. The forward portions 18a and 19a of laterally extending stops 18 and 19 aid in reforming the surgical staple 49 in one plane.

When the surgical staple 49 has been extracted from the skin 47, it can be dislodged from anvil 21 and blade 29 simply by causing upper handle 2 and lower handle 3 to return to their open positions. This will release the reformed and extracted surgical staple.

The provision of loops 14 and 35 on upper handle 2 and lower handle 3, respectively, tend to lend stability to the extractor and make its manipulation easier. Stops 15 and 36 give the surgeon a positive tactile feedback when the staple has been properly reformed. These stops also ensure that each staple will be identically reformed.

Finally, it will be evident that the extractor of the present invention can be manufactured inexpensively, and lends itself well to being manufactured as a single-use, disposable tool.

It will be understood by one skilled in the art that in the foregoing description and in the claims which follow, terms such as "upper", "lower", "vertical", and "horizontal", are used for purposes of clarity of description, in conjunction with the figures. The operator may, of course, hold the extractor in any appropriate orientation during the extracting process.

Modifications may be made in the invention without departing from the spirit of it.

What is claimed is:

1. A manually actuated extractor for a surgical staple of the type having, when implanted in the skin of a patient, an exposed crown and opposed L-shaped skin-engaging legs, said extractor comprising an upper handle and a lower handle each having a forward and a rearward end, said handles being pivotally joined together near their forward ends and being manually shiftable between open and closed positions, said upper handle terminating at its forward end in a pair of thin, laterally extending stop members with a slot located therebetween, said laterally extending stop members having coplanar staple leg-contacting forward portions lying at an obtuse angle to said upper handle, a thin, U-shaped anvil comprising a base portion and substantially parallel legs, with each of said anvil legs extending to and joining said forward portion of one of said laterally extending stop members, said anvil legs being located to either side of said slot, said anvil being substantially coplanar with said stop member forward portions which extend laterally of said anvil legs, said lower handle terminating at its forward end in a thin blade, said blade being shiftable by said lower handle such that when said handles are shifted from said open to said closed position, said blade shifts from a normal position extending through said slot and lying above said anvil downwardly through said U-shaped anvil between said anvil legs to a staple reforming position therebelow, there being clearance between said blade and each of said anvil legs at least equal to the maximum cross sectional dimension of said staple crown, whereby when said anvil is slipped beneath the crown of a staple formed and implanted in the skin of a patient, with said staple legs being contacted by said forward portions of said laterally extending stop members to assure proper alignment of the extractor with respect to said staple, and said handles are shifted to their closed position shifting said blade to its staple reforming position, said crown of said staple will be reformed into a U-shape causing said L-shaped legs to shift upwardly and outwardly enabling them to be lifted by said extractor from the skin of the patient.

2. The extractor claimed in claim 1 wherein each of said handles terminates at its rearward end in a scissors-like loop.

3. The extractor claimed in claim 1 wherein said anvil base portion is V-shaped.

4. The extractor claimed in claim 1 wherein said upper handle has a downwardly depending upper stop terminating in an abutment surface and said lower handle has an upwardly extending lower stop terminating in an abutment surface, said stops being so positioned on their respective upper and lower handles as to have their abutment surfaces in contact with each other when said handles are in said closed position to determine said closed position and to determine said staple reforming position of said blade.

5. The extractor claimed in claim 1 wherein said slot has an upper end contactable by said blade to determine said open position of said handles and said normal position of said blade.

6. The extractor claimed in claim 1 including means to bias said handles to said open position and said blade to said normal position.

7. The extractor claimed in claim 1 including a pair of shallow aligned notches, each notch located at the juncture of one of said anvil legs and the forward portion of one of said laterally extending stop members from which it extends, said aligned notches being configured to receive said crown of said implanted surgical staple when said anvil is slipped therebeneath.

8. The extractor claimed in claim 1 wherein the upper opposed edges of said anvil legs adjacent said laterally extending stop member forward portions are rounded.

9. The extractor claimed in claim 1 wherein said upper handle comprises a forward metallic portion and a rearward plastic portion, said upper handle forward metallic portion terminating at its forward end in said laterally extending stop members and said anvil, said upper handle plastic portion comprising an elongated shank affixed at its forward end to the rearward end of said upper handle metallic portion and constituting a continuation thereof, said upper handle plastic portion terminating at its rearward end in a loop engagable by the thumb of an operator of said extractor, said lower handle comprising a forward metallic portion and a rearward plastic portion, said lower handle metallic portion terminating at its forward end in said blade, said lower handle plastic portion comprising an elongated shank affixed at its forward end to the rearward end of said lower handle metallic portion and constituting a continuation thereof, said lower handle plastic portion terminating at its rearward end in a loop engagable by the finger of an operator of said extractor.

10. The extractor claimed in claim 9 wherein said upper handle metallic portion has an inverted U-shaped cross section comprising a base and a pair of downwardly depending legs, said laterally extending stop members and said anvil extending forwardly of said upper handle metallic portion base and being an integral, one-piece part thereof, one of said legs of said upper handle metallic portion having an extension extending rearwardly of said upper handle metallic portion, said shank of said upper handle plastic portion having a longitudinal cavity receiving said extension and means to maintain said extension therein, said lower handle metallic portion having a U-shaped cross section comprising a base and a pair of laterally extending legs, said blade extending forwardly of said lower handle metallic portion base and comprising an integral, one-piece part thereof, said last mentioned base terminating at its rearward end in an extension, said shank of said lower handle plastic portion having a longitudinal cavity receiving said last mentioned extension and means to maintain said last mentioned extension therein, said forward end of said lower handle metallic portion being located between said legs of said upper handle metallic portion near said forward end thereof, said blade and said upper handle metallic portion having coaxial perforations therein, a rivet mounted in said coaxial perforations to pivotally join said upper and lower handles together, and a plastic insert located between the legs of said lower handle metallic portion and surrounding said rivet.

11. The extractor claimed in claim 10 wherein said upper handle plastic portion has a downwardly depending upper stop located at the juncture of said shank and loop thereof, said upper stop terminating in an abutment surface, said lower handle plastic portion having an upwardly extending lower stop located at the juncture of said shank and loop thereof, said lower stop terminating in an abutment surface, said stops having their abutment surfaces in contact with each other when said handles are in their closed position to determine said close position and said staple reforming position of said blade.

12. The extractor claimed in claim 11 wherein said slot has an upper end contactable by said blade to determine said open position of said handles and said normal position of said blade.

13. The extractor claimed in claim 12 wherein said anvil base portion is V-shaped.

14. The extractor claimed in claim 12 including means to bias said handles to said open position and said blade to said normal position.

15. The extractor claimed in claim 14 including a pair of shallow aligned notches, each notch located at the juncture of one of said anvil legs and the forward portion of one of said laterally extending stop members from which it extends, said aligned notches being configured to receive said crown of said implanted surgical staple when said anvil is slipped therebeneath.

16. The extractor claimed in claim 14 wherein the upper opposed edges of said anvil legs adjacent said laterally extending stop member forward portions are rounded.

* * * * *